(12) United States Patent
Pernot et al.

(10) Patent No.: US 12,408,890 B2
(45) Date of Patent: Sep. 9, 2025

(54) 3-D ULTRASOUND CORONAROGRAPHY, A NON-IONIZING AND NON-INVASIVE TECHNOLOGY FOR MULTI-SCALE ANATOMICAL AND FUNCTIONAL IMAGING OF CORONARY CIRCULATION

(71) Applicants: INSERM (INSTITUT NATIONAL DE LA SANTÉ ET DE LA RECHERCHE MÉDICALE), Paris (FR); Centre National de la Recherche Scientifique (CNRS), Paris (FR); Ecole Superieure de Physique et de Chimie Industrielles de la Ville de Paris, Paris (FR)

(72) Inventors: Mathieu Pernot, Paris (FR); Mickael Tanter, Paris (FR); Clément Papadacci, Paris (FR); Oscar Demeulenaere, Paris (FR)

(73) Assignees: INSERM (INSTITUT NATIONAL DE LA SANTÉ ET DE LA RECHERCHE MÉDICALE), Paris (FR); CENTRE NATIONAL DE LA RECHERCHE SCIENTIFIQUE—CNRS, Paris (FR); ECOLE SUPERIEURE DE PHYSIQUE ET DE CHIMIE INDUSTRIELLES DE LA VILLE DE PARIS, Paris (FR)

( * ) Notice: Subject to any disclaimer, the term of this patent is extended or adjusted under 35 U.S.C. 154(b) by 390 days.

(21) Appl. No.: 17/996,094

(22) PCT Filed: Apr. 13, 2021

(86) PCT No.: PCT/EP2021/059534
§ 371 (c)(1),
(2) Date: Oct. 13, 2022

(87) PCT Pub. No.: WO2021/209435
PCT Pub. Date: Oct. 21, 2021

(65) Prior Publication Data
US 2023/0225698 A1    Jul. 20, 2023

(30) Foreign Application Priority Data
Apr. 14, 2020  (EP) .................................. 20169453

(51) Int. Cl.
*A61B 8/06*     (2006.01)
*A61B 8/00*     (2006.01)
*A61B 8/08*     (2006.01)

(52) U.S. Cl.
CPC .............. *A61B 8/06* (2013.01); *A61B 8/488* (2013.01); *A61B 8/5223* (2013.01); *A61B 8/0883* (2013.01)

(58) Field of Classification Search
CPC ......... A61B 8/06; A61B 8/488; A61B 8/5223; A61B 8/0883
See application file for complete search history.

(56) References Cited

U.S. PATENT DOCUMENTS

| 2010/0049052 | A1  | 2/2010 | Sharf et al. |
| 2016/0129233 | A1* | 5/2016 | Hoffmann ................ A61B 8/08 604/22 |

(Continued)

FOREIGN PATENT DOCUMENTS

| CN | 110881999 A | 3/2020 |
| JP | 2017015037 A | 9/2017 |

(Continued)

OTHER PUBLICATIONS

Maresca et al.; "Noninvasive Imaging of the Coronary Vasculature Using Ultrafast Ultrasound"; Cardiovascular Imaging, vol. 11, No. 6, Jun. 1, 2018, pp. 798-808.

(Continued)

*Primary Examiner* — Chao Sheng
(74) *Attorney, Agent, or Firm* — WCF IP

(57) ABSTRACT

The present invention relates to the field of ultrasounds and imagining of the coronary blood flow of the heart. Patients with coronary microvascular dysfunction (CMD) have poor prognostic with significantly higher rates of cardiovascular events, including hospitalization for heart failure, sudden cardiac death, and myocardial infarction (MI). Despite the urgent clinical need, there are no non-ionizing and non-invasive techniques available in clinic to directly visualize the coronary microvasculature and assess the local coronary microvascular system. Flow imaging remains a difficult task to perform in the heart because of the fast movements of this organ. In order to overcome the limitations of actual imaging methods for the coronary blood flow, the inventors proposed an ultrasound ultrafast imaging method that automatically detect the time periods in which the myocardium velocity is low and estimate the coronary flow velocity and the tissue velocity from the same data acquisition.

15 Claims, 6 Drawing Sheets

(56) References Cited

U.S. PATENT DOCUMENTS

| | | |
|---|---|---|
| 2017/0252000 A1 | 9/2017 | Fukuda et al. |
| 2018/0028154 A1 | 2/2018 | Zhai |
| 2019/0223828 A1 | 7/2019 | Torp et al. |
| 2020/0060652 A1 | 2/2020 | Dahl et al. |
| 2020/0077982 A1 | 3/2020 | Duncan et al. |

FOREIGN PATENT DOCUMENTS

| | | |
|---|---|---|
| JP | 2019526350 A | 9/2019 |
| WO | 2019/158741 A1 | 8/2019 |

OTHER PUBLICATIONS

Papadacci et al.; "4D simultaneous tissue and blood flow Doppler imaging: revisiting cardiac Doppler index with single heart beat 4D ultrafast echocardiography"; Physics in Medicine and Biology, vol. 64, No. 8, Apr. 10, 2019, p. 85013.

Provost et al.; "3D ultrafast ultrasound imaging"; Physics in Medicine and Biology, vol. 59, No. 19, Sep. 10, 2014, entire document.

Correia et al.; "4D ultrafast ultrasound flow imaging: quantification of arterial volumetric flow rate in a single heartbeat"; Physics in Medicine and Biology, vol. 61, No. 23, Nov. 3, 2016, entire document.

* cited by examiner

3-D ULTRASOUND CORONAROGRAPHY, A NON-IONIZING AND NON-INVASIVE TECHNOLOGY FOR MULTI-SCALE ANATOMICAL AND FUNCTIONAL IMAGING OF CORONARY CIRCULATION

FIELD

Background

Coronary circulation is responsible for cardiac perfusion and modifications of coronary flow have serious consequences on the heart's performance, as observed in the case of a stable angina or myocardial infarction. The coronary vasculature is organized in three compartments. The first is made of the epicardial coronary arteries, which run along the heart's surface and exhibit diameters ranging from a few millimeters down to 500 µm. The second includes the pre-arterioles, which penetrate the myocardium from the epicardium to the endocardium and exhibit diameters ranging from 500 µm down to 100 µm. The third corresponds to the coronary microvasculature, which exhibit vessel diameters below 100 µm [1].

To date, the epicardial coronary vasculature is the only compartment that can be imaged in vivo in humans with current angiography techniques [1,2] such as X-ray [3], Computed Tomography Angiography (CTA) [4] or Cardiac Magnetic Resonance (CMR) Imaging [5]. As a consequence, cardiology practice has been centered on focal macroscopic coronary artery disease. For instance, Invasive Coronary Angiography (ICA) [3] with catheterization remains today the reference technique for investigating coronary lesions in case of suspected ischemia. ICA provides both anatomic analysis of major epicardial stenosis but also global functional assessment based on fractional flow reserve (FFR). The evaluation of FFR is indeed a major tool for clinical decision-making in ischemic heart disease [2,6] and subsequent pharmacologic or invasive treatment via percutaneous coronary interventions or surgery [7].

In many patients, early manifestations of coronary artery disease (CAD) are microvascular disease and it is now recognized that coronary microvascular dysfunction, i.e., including pre-arterioles, is an important marker of myocardial ischemia [1,6], which however remains challenging to assess in clinical practice.

Indeed, clinical guidelines in the management of stable ischemic heart disease only consider coronary microvascular dysfunction after excluding signs of epicardial disease [8]. A large number of patients with angina symptoms and ischemia on stress testing have a normal coronary angiogram [9]. Current evidence shows that a significant portion of these patients have coronary microvascular dysfunction (CMD), also known as microvascular angina [9]. Patients with CMD have poor prognostic with significantly higher rates of cardiovascular events, including hospitalization for heart failure, sudden cardiac death, and myocardial infarction (MI).

Despite the urgent clinical need, there are no techniques available in clinic, to directly visualize the coronary microvasculature and assess the local coronary microvascular system. Up to date, only global indirect measurements through functional testing (PET, CMR and contrast echocardiography) provide hemodynamic information such as Myocardial Blood Flow (MBF) and Coronary Flow Reserve (CFR) in response to the vasodilator adenosine [1].

However, despite the improvement of radiation dose management, the cumulative radiation exposure of ionizing modalities remains associated with risks of cancers [10]. The risk is particularly important in paediatric patients such as children with congenital or acquired heart disease that can be exposed to relatively high lifetime cumulative doses of ionizing radiation from necessary medical imaging procedures [11] including radiography, fluoroscopic procedures including diagnostic and interventional cardiac catheterizations, electrophysiology examinations, cardiac computed tomography (CT) studies, and nuclear cardiology examinations.

Flow imaging remains a difficult task to perform is a fast moving organ like the heart. The sensitivity of conventional ultrasound Doppler imaging has long remained limited for imaging small vessels with low flow velocities (<1 cm/s) and the overlap of tissue and blood motion in this range of velocities makes the separation of tissue and blood signal challenging. In the recent years, ultrafast Doppler imaging has allowed a tremendous increase in the sensitivity of blood flow imaging. This technique was shown capable to detect small blood flow changes in the brain due to the neurovascular coupling and therefore perform functional brain imaging in anesthetized and awake small animals for research in neuroscience [12]. Sensitivity was further increased by the development of new clutter filters adapted to ultrafast imaging, such as the spatio-temporal singular value decomposition [13]. However, in cardiac applications, ultrasound Doppler imaging of coronary blood flow still remains limited because of the fast movements of the heart.

It has been demonstrated that ultrafast Doppler imaging enables to limit the impact of a part of said movements and allows increasing the sensitivity of Doppler imaging [14] but Doppler imaging remains impossible during the fast moving phases of the heart.

In order to overcome the limitations of actual imaging methods for the coronary blood flow, the inventors adapted the 4-D (3-D+time) ultrasound ultrafast imaging method recently proposed [15] to automatically detect the time periods in which the myocardium velocity is low, and to estimate the flow velocity and the tissue velocity from the same data acquisition.

Therefore, a non-invasive, non-ionizing technique for imaging the coronary blood flows at macro and microscopic scales at the bedside of the patient is provided.

SUMMARY OF THE INVENTION

The scope of the invention is defined by the claims. Any subject-matter falling outside the scope of the claims is provided for information purposes only.

It is hereby disclosed a non-invasive and non-ionizing imaging method to enhance the direct imaging of the coronary blood flows and the imaging of the anatomy and function of coronary vessels at the macro- and microscopic scales from epicardial to endocardial regions.

Therefore, an imaging method, an imaging device and a computer-readable medium are provided, for a non-ionizing, non-invasive anatomical and functional imaging of coronary vessels at macro and microscopic scales.

LIST OF ABBREVIATIONS

CAD=Coronary Artery Disease
CFR=Coronary Flow Reserve
CMD=Coronary Microvascular Dysfunction
CMR=Cardiac Magnetic Resonance
CT=Computed Tomography
CTA=Computed Tomography Angiography DSP=Digital Signal Processor
ECG=Electrocardiogram
FFR=Fractional Flow Reserve
ICA=Invasive Coronary Angiography
MBF=Myocardial Blood Flow
MI=Myocardial Infarction
PET=Positron Emission Tomography
SVD=Singular Value Decomposition
TD=Transmit Delay

BRIEF DESCRIPTION OF DRAWINGS

Other features and advantages of the disclosure appear from the following detailed description of one non-limiting example thereof, with reference to the accompanying drawings.

In the drawings.

DETAILED DESCRIPTION

In the Figures, the same references denote identical or similar elements.

Figure 1:
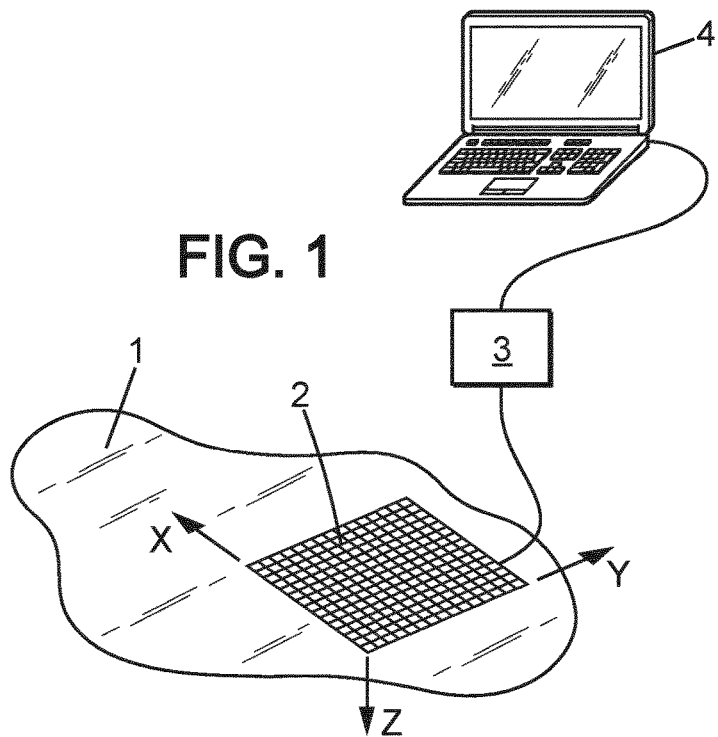
FIG. 1 is a schematic drawing showing an apparatus for 4D imaging of the heart.
Figure 2:
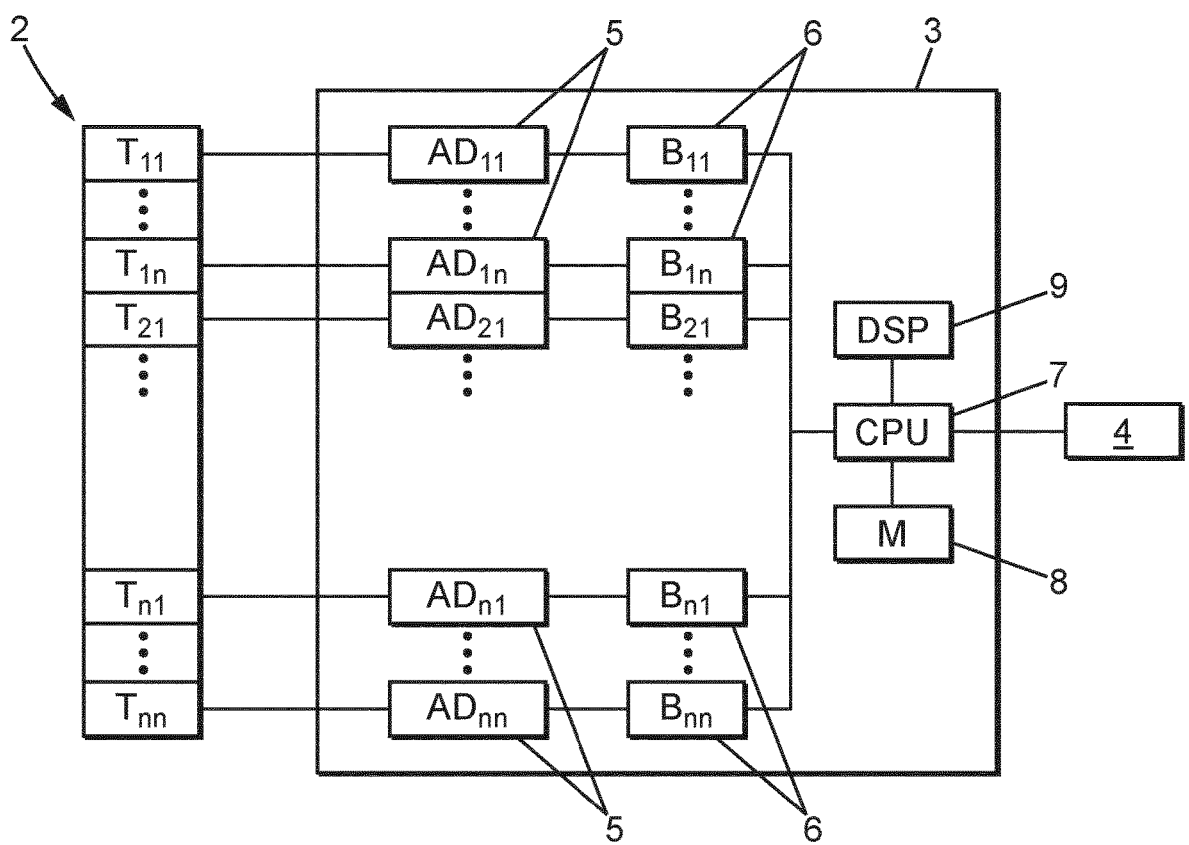
FIG. 2 is a block diagram showing part of the apparatus of FIG. 1.

The apparatus shown on FIGS. 1 and 2 is adapted to ultrafast 4D ultrasound imaging of the heart of a living being 1, for instance a mammal and in particular a human.

The apparatus may include for instance at least a 2D array ultrasonic probe 2 and a control system.

The 2D array ultrasonic probe 2 may have for instance a few hundreds to a few thousands transducer elements $T_{ij}$, with a pitch lower than 1 mm. The 2D array ultrasonic probe 2 may have n*n transducer elements disposed as a matrix along two perpendicular axes X, Y, transmitting ultrasound waves along an axis Z which is perpendicular to the XY plane. In one specific example, the 2D array ultrasonic probe 2 may have 1024 transducer elements $T_{ij}$ (32*32), with a 0.3 mm pitch. The transducer elements may transmit for instance at a central frequency comprised between 1 and 10 MHz, for instance of 3 MHz.

The control system may for instance include a specific control unit 3 and a computer 4. In this example, the control unit 3 is used for controlling 2D array ultrasonic probe 2 and acquiring signals therefrom, while the computer 4 is used for controlling the control unit 3, generating 3D image sequences from the signals acquired by control unit 3 and determining quantification parameters therefrom. In a variant, a single electronic device could fulfill all the functionalities of control unit 3 and computer 4.

As shown on FIG. 2, control unit 3 may include for instance:
- n*n analog/digital converters 5 ($AD_{ij}$) individually connected to the n transducers $T_{ij}$ of 2D array ultrasonic probe 2;
- n*n buffer memories 6 ($B_{ij}$) respectively connected to the n*n analog/digital converters 5;
- a central processing unit 7 (CPU) communicating with the buffer memories 6 and the computer 4;
- a memory 8 (MEM) connected to the central processing unit 7;
- a digital signal processor 9 (DSP) connected to the central processing unit 7.

The apparatus may operate as follows.

Figure 4:
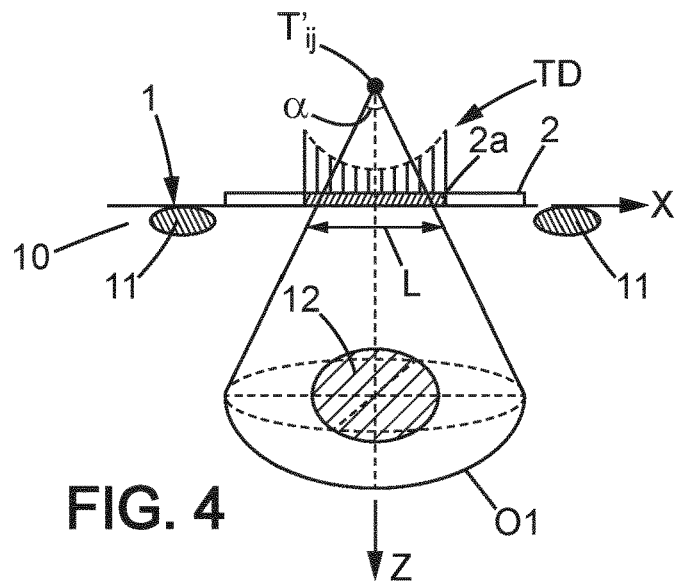
FIG. 4 illustrates the transmission of a divergent ultrasound wave in the heart of a living being by the apparatus of FIGS. 1-2.

(a) Acquisition:

The 2D array ultrasonic probe 2 is placed on the chest 10 of the patient 1, usually between two ribs, in front of the heart 12 of the patient as shown in FIG. 4.

Because of the limited intercostal space between ribs 11 compared to the size of the heart 12 to be imaged, the 2D array ultrasonic probe 2 is controlled to transmit divergent ultrasonic waves in the chest 10, for instance spherical ultrasonic waves (i.e. having a spherical wave front O1). The control system may be programmed such that the ultrasonic waves are transmitted at a rate of several thousand ultrasonic waves per second, for instance more than 10 000 unfocussed ultrasonic waves per second.

Figure 3:
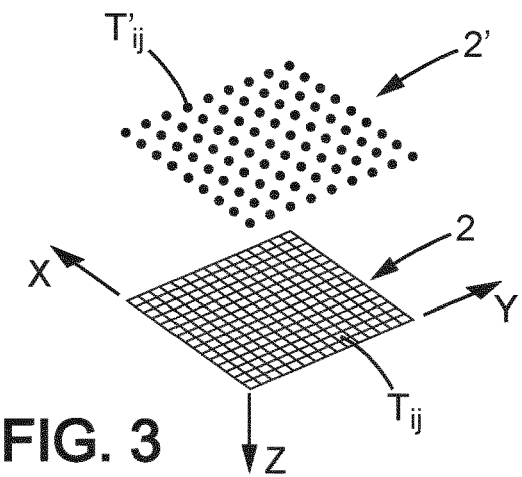
FIG. 3 is a diagram illustrating virtual sources of divergent ultrasound waves, generated by the apparatus of FIGS. 1-2.

Spherical waves can be generated by a single transducer element (with low amplitude) or more advantageously with higher amplitude by a large part of the matrix array using one or more virtual point sources $T'_{ij}$ forming a virtual array 2' placed behind of in front of the 2D array ultrasonic probe 2, as shown in FIGS. 3-4. The transmit delay TD applied by the control system to a transducer element e placed in position $$\begin{pmatrix} x_e \\ y_e \\ 0 \end{pmatrix}$$

associated to the virtual source v placed in position $$\begin{pmatrix} x_v \\ y_v \\ z_v \end{pmatrix}$$

is:

$$TD = \sqrt{z_v^2 + (x_e - x_v)^2 + (y_e - y_v)^2}/c$$

where c is the speed of sound.

For each virtual source $T'_{ij}$ used, it is possible for the control system to activate only a subset 2a of the 2D array ultrasonic probe 2, having a sub-aperture L which determines the aperture angle α of the divergent ultrasonic wave. The aperture angle α may be for instance of 90°. The imaged depth along axis Z may be about 12 to 15 cm.

It is possible to use only one virtual source $T'_{ij}$ and thus one ultrasonic wave for each 3D image of the heart, as will be explained later.

Figure 5:
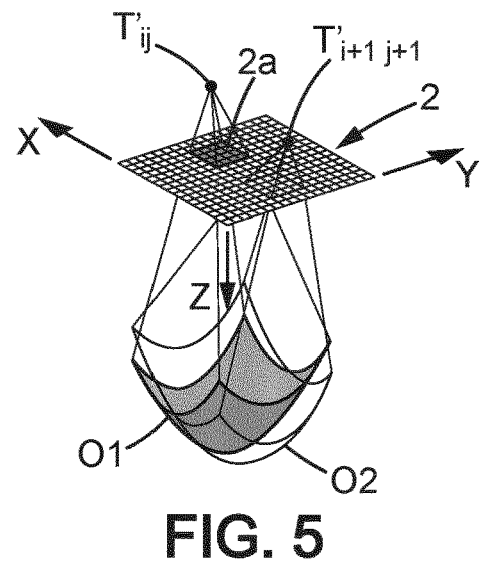
FIG. 5 illustrates the transmission of two successive divergent ultrasound waves with different directions of propagation, respectively from two virtual sources.
Figure 6:
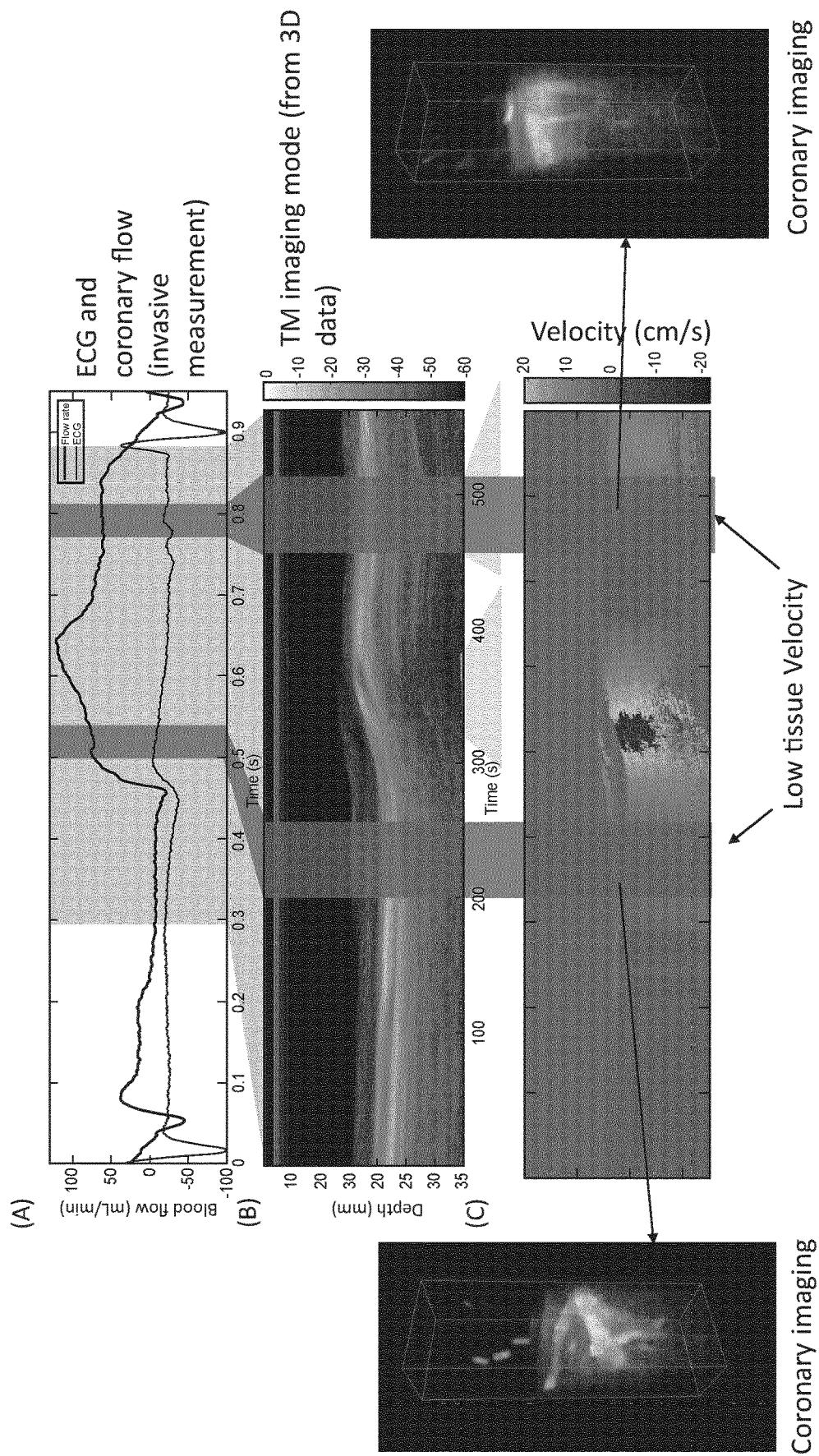
FIG. 6 illustrates myocardial wall motion during the cardiac cycle. The blood flow can be reconstructed within the two temporal windows with limited tissue velocity.
Figure 7:
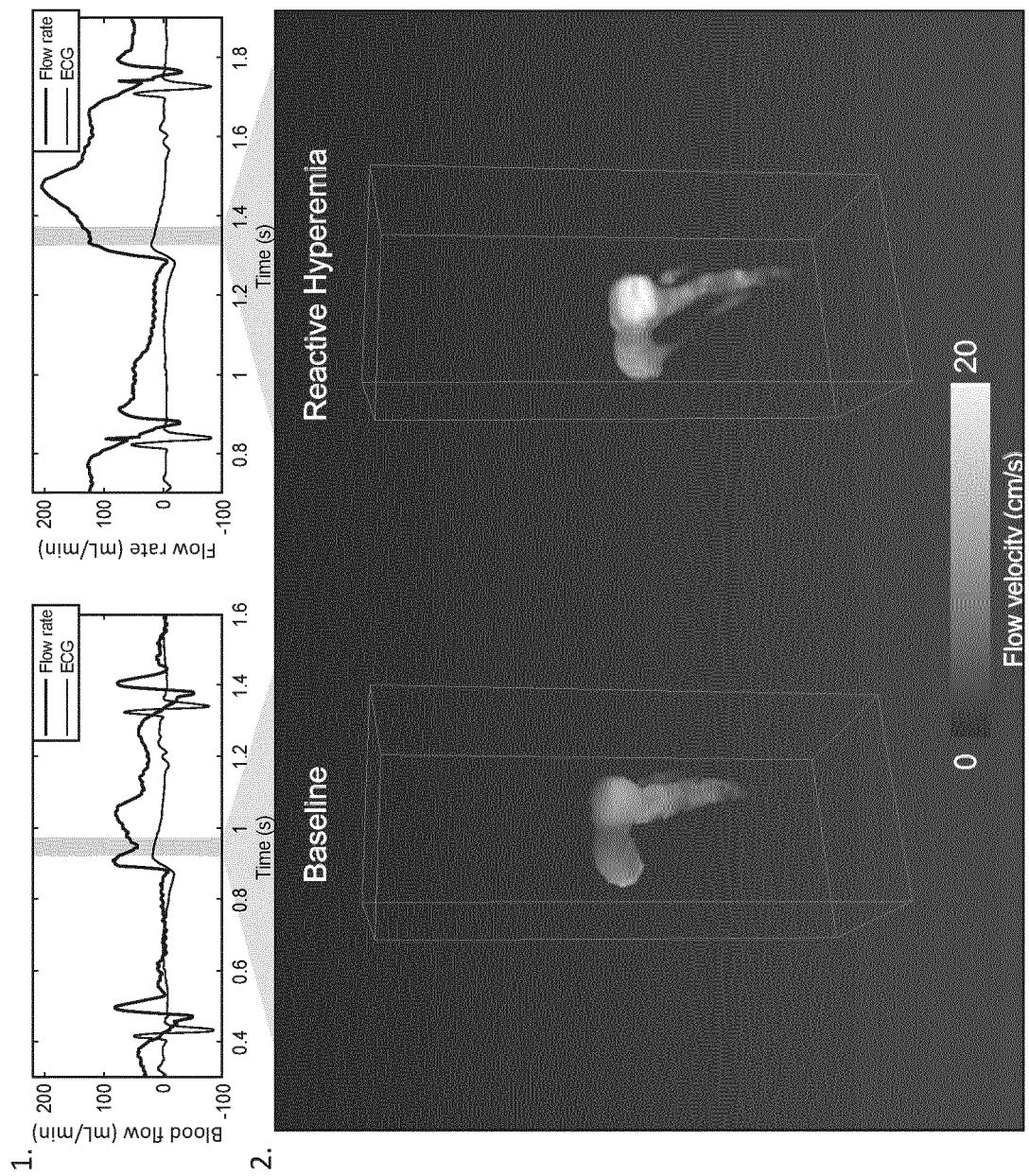
FIG. 7 illustrates an example of coronary flow velocity imaging during baseline and reactive hyperemia.
Figure 8:
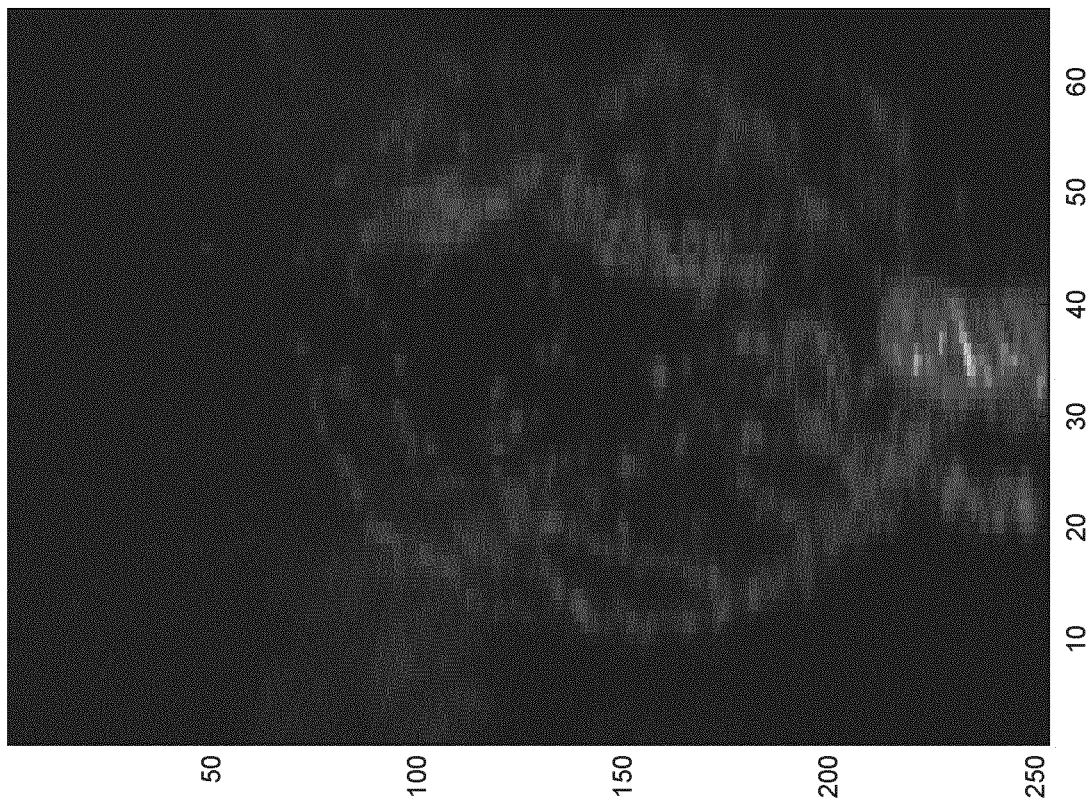
FIG. 8 shows microbubble imaging and localization (average intensity projection)
Figure 9:
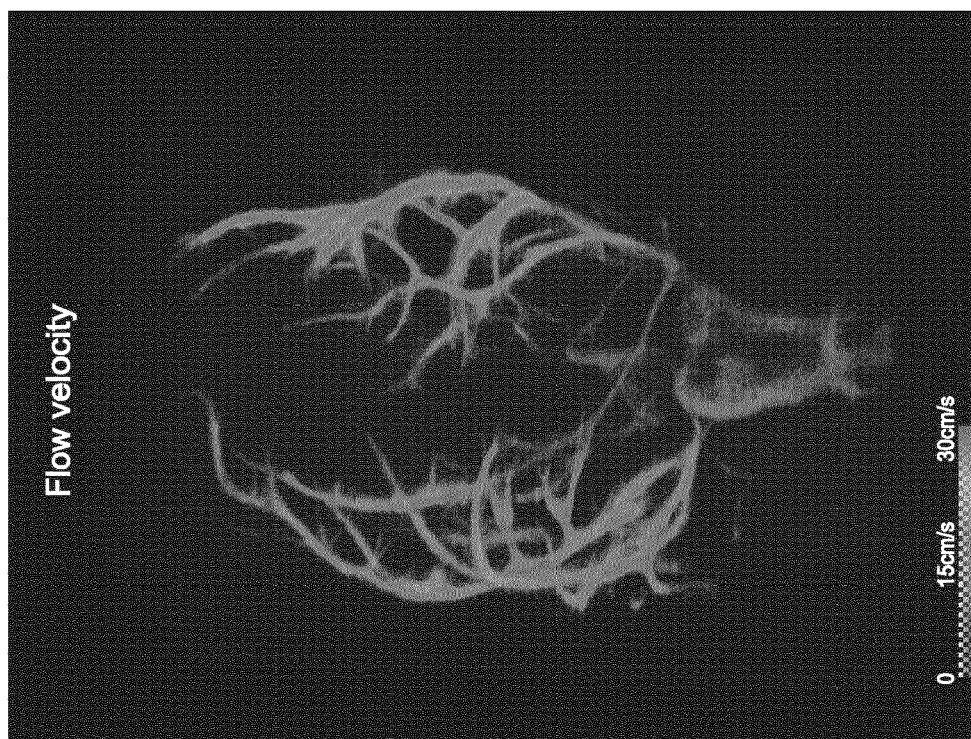
FIG. 9: shows microbubble localization and tracking with (A) the coronary artery network of an isolated heart perfused by ultrasound imaging and (B) the mapping coronary flow velocities in an isolated perfused heart.
Figure 9:
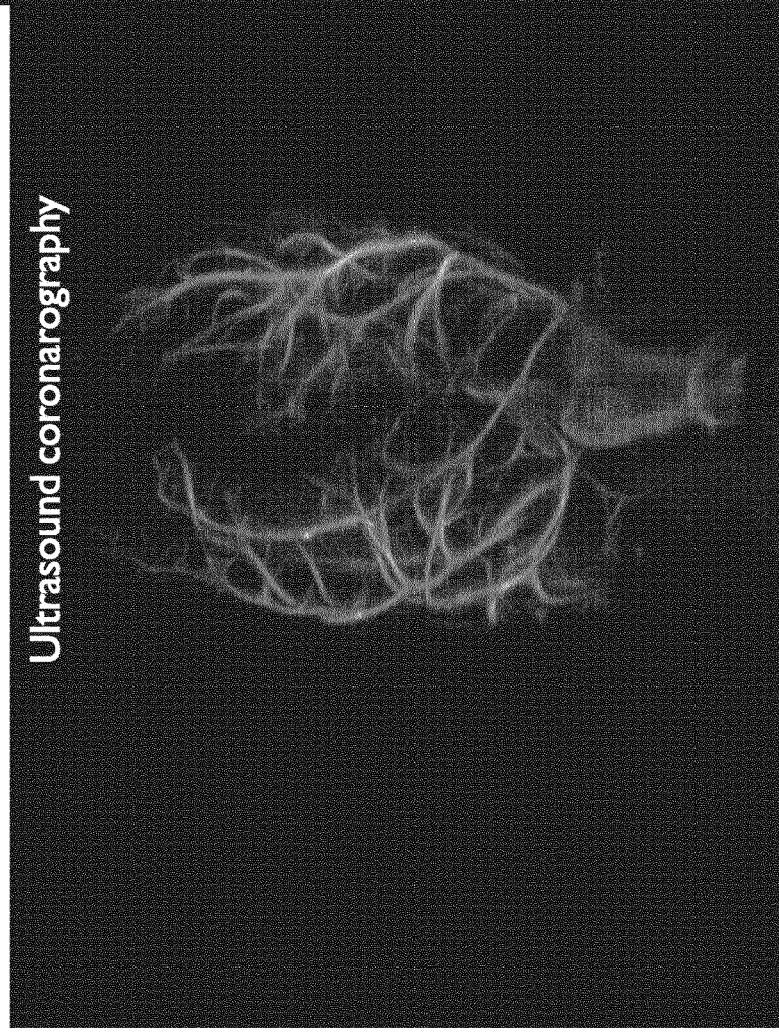

However, to enhance image resolution and contrast, it is useful to transmit the unfocused ultrasonic waves in series of successive unfocussed ultrasonic waves, the successive unfocused ultrasonic waves of each series having respectively different propagation directions: in that case, each 3D image is synthesized from the signals acquired from one of said series of successive unfocussed ultrasonic waves as will be explained later. The successive ultrasonic waves of each series may be obtained by varying the virtual source $T_{ij}$ from one wave to the other, thus varying the wave front O1, O2 etc., as shown in FIG. 5. Each series may include for instance 1 to 81 successive ultrasonic waves of different directions, for instance 3 to 25 successive ultrasonic waves of different directions, for instance 5 to 20 successive ultrasonic waves of different directions, for instance 10 to 20 successive ultrasonic waves of different directions.

In all cases, after each ultrasonic wave is transmitted, backscattered echoes are acquired by said 2D array ultrasonic probe (sampled for instance with a sampling rate of 12 MHz) and memorized. This raw data (also usually called RF data or radiofrequency data) is the used to generate a sequence of 3D images.

The duration of acquisition may be comprised between 10 ms and a few cardiac cycles, for instance at least one part of the cardiac cycle (for instance the diastole or systole, preferably the diastole, or one cardiac cycle) and less than 10 cardiac cycles (for instance less than 5 cardiac cycles). Such duration may be for instance comprised between 1 s and 10 s (for instance less than 5 s). In a specific example, such duration is around 1.5 s.

An electrocardiogram (ECG) may be co-recorded during the acquisition.

(b) Imaging:

After receiving the backscattered echoes, a parallel beamforming may be directly applied by the control system to reconstruct the 3D image from each single ultrasonic wave. Delay and sum beamforming can be used in the time domain or in the Fourier domain. In the time domain, the delays applied on the signal received by each transducer element e to reconstruct a voxel placed in $$\begin{pmatrix} x \\ y \\ z \end{pmatrix}$$

is the sum of the forward propagation time from the virtual source v to the voxel and the backscattered propagation time to the transducer element e:

Delay=forward delay+Backscattered delay

Forward delay=$\sqrt{(z-z_v)^2+(x-x_v)^2+(y-y_v)^2}/c$

Backscattered delay=$\sqrt{z^2+(x_e-x)^2+(y_e-y)^2}/c$

Another possibility is to use Fourier-domain imaging (spatial frequencies, k-space).

In case the ultrasonic waves are transmitted by series of ultrasonic waves having respectively different propagation directions as explained above, each image can be obtained by the control system through known processes of synthetic imaging. Voxels are beamformed using delay-and-sum algorithms for each virtual source and subsequently coherently compounded to form a final, high quality 3D image. Details of such synthetic imaging can be found for instance in:

Montaldo, G., Tanter, M., Bercoff, J., Benech, N., Fink, M., 2009. *Coherent plane-wave compounding for very high frame rate ultrasonography and transient elastography.* IEEE Trans. Ultrason. Ferroelectr. Freq. Control 56, 489-506. doi:10.1109/TUFFC.2009.1067

Nikolov, S. I., 2001. *Synthetic aperture tissue and flow ultrasound imaging.* Orsted-DTU, Technical University of Denmark, Lyngby, Denmark.

Nikolov, S. I., Kortbek, J., Jensen, J. A., 2010. *Practical applications of synthetic aperture imaging,* in: 2010 IEEE Ultrasonics Symposium (IUS). Presented at the 2010 IEEE Ultrasonics Symposium (IUS), pp. 350-358. doi:10.1109/ULTSYM.2010.5935627

Lockwood, G. R., Talman, J. R., Brunke, S. S., 1998. *Real-time 3-D ultrasound imaging using sparse synthetic aperture beamforming.* IEEE Trans. Ultrason. Ferroelectr. Freq. Control 45, 980-988. doi:10.1109/58.710573

Papadacci, C., Pernot, M., Couade, M., Fink, M. & Tanter, M. *High-contrast ultrafast imaging of the heart.* IEEE transactions on ultrasonics, ferroelectrics, and frequency control 61, 288-301, doi:10.1109/tuffc.2014.6722614 (2014).

The framerate, i.e. the rate of 3D images in the animated sequence which is finally obtained, may be of several thousand 3D images per second, for instance 3000 to 5000 3D images per second.

(c) Determination of a Time Window:

A time window in which the tissue velocity reaches a minimum may be identified by the control system using known methods.

In specific examples, the time window in which the tissue velocity reaches a minimum can be defined as:
 the time window in which the velocity of the myocardium is less than 5 cm/s, or
 the time window that correspond to the beginning and the end of the diastole phase.

In a specific example, the time window is determined by means of electrography.

In another specific example, the time window is determined by means of a tissue motion estimation performed by the control system, using the methods described below.

(d) Blood and Tissue Velocity Computing:

Blood flow and tissue motion estimation may be performed by the control system using known methods.

For instance, the Kasai algorithm may be used to estimate motion in blood and in tissues with a half-wavelength spatial sampling (Kasai, C., Namekawa, K., Koyano, A., Omoto, R., 1985. Real-Time Two-Dimensional Blood Flow Imaging Using an Autocorrelation Technique. IEEE Trans. Sonics Ultrason. 32, 458-464. doi:10.1109/T-SU.1985.31615). Blood flow can be estimated by first applying a high-pass filter to the baseband data and then, for each individual voxel, Power Doppler may be obtained by integrating the power-spectral density, Pulsed Doppler may be obtained by computing the short-time Fourier transform, and Color Doppler maps may be obtained by estimating the first moment of the voxel-specific Pulsed-Doppler spectrogram. Power velocity integral maps can be obtained by computing the time integral of power times velocity in order to obtain images of a parameter related to flow rate. Advanced filtering such as Spatio-temporal filters based on singular value decomposition can also be used to better remove the clutter signal (Demené, C. et al. Spatiotemporal Clutter Filtering of Ultrafast Ultrasound Data Highly Increases Doppler and Ultrasound Sensitivity. IEEE transactions on medical imaging 34, 2271-2285, doi:10.1109/tmi.2015.2428634 (2015)).

In a specific example:
 4D tissue velocities may be computed by performing 1D cross-correlation to obtain volumes of tissue volume-to-volume axial displacements. A butter-worth lowpass filtering with a 60 Hz cut-off frequency was then applied on the displacements. A myocardium 3D mask (specific to the tissues of the myocardium) may be applied to remove signal outside the muscle. To display 4D tissue velocities, Amira® software may be used. In each voxel, one tissue velocity curve may be derived.

4D Color Doppler may be computed by performing an SVD filtering to remove signal from the tissue and keep only the signal from the blood flow as it is done for instance in the above publication by Demené et al. 1D axial cross-correlation pixel-per-pixel on SVD-filtered voxels may be performed to obtain Color Doppler volumes.

The myocardium may be segmented using integrated tissue velocity over the cardiac cycle and manual selection of the contour on two perpendicular 2D slices. An elliptic interpolation may be used to get the three-dimensional representation.

More generally, step (d) involves automatically computing 3D cartography of at least one parameter related to blood velocity and/or tissue velocity in said imaged volume, based on said sequence of 3D images. Said 3D cartography may consist of an animated sequence of 3D images of the computed parameter. The parameter may be blood and/or tissue velocity, or a component thereof.

(e) Locating of Points of Interest:

Depending on the quantification parameters which are sought, at least one point of interest having a predetermined property is located in the sequence of 3D images. Said at least one point of interest having a predetermined property can be automatically located by the control system or manually located by the operator.

When the quantification parameter involves the blood velocity in a certain anatomic area, the control system may automatically locate or the operator may manually locate said point of interest as a point of blood velocity in said anatomic area and in at least part of the sequence of 3D images. In a specific example, a Fourier transform over time may be performed at each voxel using a 60 sample sliding window to retrieve a spectrogram everywhere in the volume. Automatic dealiasing may be performed according to the above Demené et al. The location of point of interest may then be automatically detected by detecting the blood flow maximum.

When the quantification parameter involves tissue velocity at a certain anatomic position in the heart, the control system may automatically locate or the operator may manually locate said anatomic position in the sequence of 3D images. Such automatic location may be done according to an anatomic model of the heart memorized in computer 4, or by selecting a point in the tissues.

When the quantification parameter involves a minimum tissue velocity in a certain anatomic area, the control system may automatically locate or the operator may manually locate said anatomic area in the sequence of 3D images and said point of interest as a point of minimum tissue velocity in said anatomic area in the sequence of 3D images. For instance, when the minimum tissue velocity of the myocardium has to be computed, the system determines a point of the myocardium having the minimum velocity in the image sequence myocardium.

(f) Quantification

The desired quantification parameter(s) can then be computed by the control system (and in particular by computer 4) based on the previously determined point(s) of interest, and based on the peak blood or tissue velocity of such point of interest.

It should be noted that:

at step of locating points of interest (step (e)), said at least one point of interest is located based solely on said 3D cartography and its temporal profile;

and at step of quantification (step (f)), said at least one velocity is automatically determined at said at least one point of interest based solely on said 3D cartography and its temporal profile.

More generally, in the present disclosure the coronary blood flows can be localized using only the spatial and temporal velocity information without any additional anatomic information.

The point and interest and the velocity at this point of interest are thus determined without need of anatomical image, in particular without need of a B-mode anatomical image, thanks to the fact that the present method involves determining the 3D cartography of velocity in the whole imaged volume. Thus, the whole method of the present disclosure need no B-mode imaging, and more generally no anatomical imaging, which enables quicker results of the present method.

Therefore, a method for imaging coronary blood flow of the heart of a living being is provided, said method including at least the following steps:

Step a) an acquisition step wherein unfocused ultrasonic waves are transmitted in the heart by a 2D array ultrasonic transducer and raw data from backscattered ultrasonic waves are acquired by said 2D array ultrasonic transducer;

Step b) an imaging step wherein a sequence of N 3D volumetric coronary blood flow images of said living heart is generated from said raw data, said sequence of 3D images forming an animation showing movements of an imaged volume of the heart;

Step c) a determination step wherein at least one time window is determined, for which the motion of the heart is minimum;

Step d) a computing step wherein a 3D cartography of at least one parameter related to coronary blood flow velocity is automatically computed in said imaged volume, based on the sequence of N 3D coronary blood flow images corresponding to the at least one time window identified in step c);

Step e) a locating step wherein at least one point of interest having a predetermined property is located in said sequence of N 3D coronary blood flow images corresponding to the at least one time window identified in step c), based solely on the 3D cartography of step d);

Step f) a quantification step wherein the coronary blood flow velocity is automatically determined at the at least one point of interest of step e) and a predetermined quantification parameter is automatically computed, involving said coronary blood flow velocity; said coronary blood flow velocity being automatically determined at said at least one point of interest based solely on the 3D cartography of step d).

The method may further include one and/or other of the following features:

the least one time window of determination step c) is determined by means of electrocardiography;

the determination step c) comprises the following steps:

Step i) an imaging step wherein a sequence of N 3D volumetric tissue images of said living heart are generated from the raw data of step a), said sequence of 3D images forming an animation showing movements of an imaged volume of the heart, Step ii) a computing step wherein a 3D cartography of at least one parameter related to heart tissue velocity is automatically computed in said imaged volume, based on said sequence of N 3D volumetric tissue images showing movements of an imaged volume of the heart, Step iii) a motion estimation step of the heart tissue wherein at least one point of interest having a predetermined property is located in said sequence of N 3D volumetric tissue images, based solely on the 3D cartography of step ii), and wherein the tissue velocity at said at least one point of interest is automatically determined; and Step iv) a determination step wherein said time window is determined, for which the tissue velocity quantified in step iii) reaches a minimum velocity;

the tissue imaging step of step i) is performed simultaneously with the flow imaging step of step b);

the minimum velocity of step iv) is less than 5 cm/s;

steps a) to f) are repeated for every cardiac cycle;

the at least one time window of step c) correspond to the beginning and the end of the diastole phase;

the quantification parameter of step f) is chosen amongst flow, maximum speed, average speed or temporal speed profile;

a tracking step wherein microbubbles or ultrasound contrast agents are tracked and their trajectory and speed is determined, in a patient that has been previously administrated with microbubbles or ultrasound contrast agents injected in his vascular system;

the tissue motion estimation is performed by means of Doppler estimator or speckle tracking;

the coronary blood flow 3D cartography is performed by means of Doppler energy imaging, Doppler color imaging or speckle tracking;

the tissue motion during the time window of step c) is estimated and a motion correction is applied, the estimation of the tissue motion comprising the following steps:

Step 1) an imaging step wherein a sequence of N 3D volumetric tissue images of said living heart are generated from the raw data of step a) corresponding to the time window of step c), said sequence of 3D images forming an animation showing movements of an imaged volume of the heart during the time window of step c), Step 2) a computing step wherein a 3D cartography of at least one parameter related to heart tissue velocity is automatically computed in said imaged volume, based on said sequence of N 3D volumetric tissue images showing movements of an imaged volume of the heart during the time window of step c), and Step 3) a motion estimation step of the heart tissue wherein at least one point of interest having a predetermined property is located in said sequence of N 3D volumetric tissue images, based solely on the 3D cartography of step 2), and wherein the tissue velocity at said at least one point of interest is automatically determined;

an automatic image registration is performed with the successive coronary blood flow 3D cartographies computed;

the bubble or ultrasound contrast agents tracking step consists of spatiotemporal filtering or machine learning;

the density of the coronary vessels is automatically quantified;

the blood volume perfused by volume unit is automatically quantified;

a stenosis is automatically detected by means of an acceleration of the blood flow velocity;

the coronary flow reserve index is obtained by estimating the variation of coronary blood flow velocity in a patient that has been previously administrated with a vasodilator substance;

an automatic segmentation step of the central cavity;

the at least one point of interest having a predetermined property of the locating step e) is automatically located or manually located by the operator;

the at least one point of interest having a predetermined property of the motion estimation step iii) is automatically located or manually located by the operator;

the at least one point of interest having a predetermined property of the motion estimation step 3) is automatically located or manually located by the operator.

Besides, it is also disclosed an apparatus for 4D imaging coronary blood flow of the heart of a living being according to the method described above, said apparatus including at least a 2D array ultrasonic probe (2) and a control system (3, 4) configured to:

(a) transmit unfocused ultrasonic waves in the heart by a 2D array ultrasonic transducer and acquire raw data from backscattered ultrasonic waves through said 2D array ultrasonic transducer;

(b) generate a sequence of N 3D volumetric coronary blood flow images of said living heart from said raw data, said sequence of 3D images forming an animation showing movements of an imaged volume of the heart;

(c) identify at least one time window for which the motion of the heart is minimum;

(d) automatically compute a 3D cartography of at least one parameter related to coronary blood flow velocity in said imaged volume, based on the sequence of N 3D coronary blood flow images corresponding to the at least one time window identified in (c);

(e) locate at least one point of interest having a predetermined property in said sequence of N 3D coronary blood flow images corresponding to the at least one time window identified in (c), based solely on the 3D cartography of (d);

(f) automatically determine the coronary blood flow velocity at the at least one point of interest of (e) based solely on the 3D cartography of (d) and automatically compute a predetermined quantification parameter involving said coronary blood flow velocity.

The apparatus may further include one and/or other of the following features:

in (c), the apparatus is configured to:
(i) generate a sequence of N 3D volumetric tissue images of said living heart from the raw data of (a), said sequence of 3D images forming an animation showing movements of an imaged volume of the heart, (ii) automatically compute a 3D cartography of at least one parameter related to heart tissue velocity in said imaged volume, based on said sequence of N 3D volumetric tissue images showing movements of an imaged volume of the heart, (iii) locate at least one point of interest having a predetermined property in said sequence of N 3D volumetric tissue images, based solely on the 3D cartography of (ii), and automatically determine the tissue velocity at said at least one point of interest; and (iv) determine said time window for which the tissue velocity quantified in (iii) reaches a minimum velocity.

in (c), the apparatus is configured to determine the at least one time window of (c) by means of electrocardiography.

It is also disclosed a computer-readable medium for 4D imaging coronary blood flow of the heart of a living being according to the method described above, said computer-readable medium comprising instructions which, when executed by a computer, cause the computer to carry out the following steps:

Step a) transmitting unfocused ultrasonic waves in the heart by a 2D array ultrasonic transducer and acquiring raw data from backscattered ultrasonic waves through said 2D array ultrasonic transducer;

Step b) generating a sequence of N 3D volumetric coronary blood flow images of said living heart from said raw data, said sequence of 3D images forming an animation showing movements of an imaged volume of the heart;

Step c) identifying at least one time window for which the motion of the heart is minimum;

Step d) automatically computing a 3D cartography of at least one parameter related to coronary blood flow velocity in said imaged volume, based on the sequence of N 3D coronary blood flow images corresponding to the at least one time window identified in step c);

Step e) locating at least one point of interest having a predetermined property in said sequence of N 3D coronary blood flow images corresponding to the at least one time window identified in step c), based solely on the 3D cartography of step d);

Step f) automatically determining the coronary blood flow velocity at the at least one point of interest of step e) based solely on the 3D cartography of step d) and automatically computing a predetermined quantification parameter involving said coronary blood flow velocity.

The computer-readable medium may further include instructions which, when executed by a computer, cause the computer to carry out the following steps:

in step c), the computer is configured to carry out the following steps:
(i) generating a sequence of N 3D volumetric tissue images of said living heart from the raw data of (a), said sequence of 3D images forming an animation showing movements of an imaged volume of the heart,
(ii) automatically computing a 3D cartography of at least one parameter related to heart tissue velocity in said imaged volume, based on said sequence of N 3D volumetric tissue images showing movements of an imaged volume of the heart,
(iii) locating at least one point of interest having a predetermined property in said sequence of N 3D volumetric tissue images, based solely on the 3D cartography of (ii), and automatically determining the tissue velocity at said at least one point of interest; and
(iv) determining said time window for which the tissue velocity quantified in (iii) reaches a minimum velocity.

the computer-readable medium is configured to carry out step c) by means of electrocardiography.

Examples

In a particular example, the method for imaging coronary blood flow of the heart of a living being comprises the following steps:

Step a) an acquisition step wherein unfocused ultrasonic waves are transmitted in the heart by a 2D array ultrasonic transducer and raw data from backscattered ultrasonic waves are acquired by said 2D array ultrasonic transducer;

Step b) an imaging step wherein a sequence of N 3D volumetric tissue and N 3D volumetric coronary blood flow images of said living heart are generated from raw data of step a), said sequence of 3D images forming an animation showing movements of an imaged volume of the heart;

Step c) a determination step wherein at least one time window for which the motion of the heart is minimum is determined, comprising the following steps:
(i) a computing step wherein, based on the sequence of N 3D volumetric tissue images of step b) showing movements of an imaged volume of the heart, a 3D cartography of at least one parameter related to heart tissue velocity is automatically computed in said imaged volume,
(ii) a motion estimation step of the heart tissue wherein at least one point of interest having a predetermined property is located in said sequence of N 3D volumetric tissue images, based solely on the 3D cartography of step (i), and wherein the tissue velocity at said at least one point of interest is automatically determined; and
(iii) a determination step wherein the time window is determined when the tissue velocity quantified in step (ii) reaches a minimum velocity;

Step d) a computing step wherein a 3D cartography of at least one parameter related to coronary blood flow velocity is automatically computed in said imaged volume, based on the sequence of N 3D coronary blood flow images corresponding to the at least one time window identified in step c);

Step e) a locating step wherein at least one point of interest having a predetermined property is automatically located in said sequence of N 3D coronary blood flow images corresponding to the at least one time window identified in step c), based solely on the 3D cartography of step d);

Step f) a quantification step wherein the coronary blood flow velocity is automatically determined at the at least one point of interest of step e) and a predetermined quantification parameter is automatically computed, involving said coronary blood flow velocity; said coronary blood flow velocity being automatically determined at said at least one point of interest based solely on the 3D cartography of step d).

In another particular example, the method for imaging coronary blood flow of the heart of a living being comprises the following steps:

Step a) an acquisition step wherein unfocused ultrasonic waves are transmitted in the heart by a 2D array ultrasonic transducer and raw data from backscattered ultrasonic waves are acquired by said 2D array ultrasonic transducer;

Step b) an imaging step wherein a sequence of N 3D volumetric coronary blood flow images of said living heart is generated from said raw data, said sequence of 3D images forming an animation showing movements of an imaged volume of the heart;

Step c) a determination step wherein at least one time window for which the motion of the heart is minimum is determined, said time window being determined by means of electrocardiography, wherein the at least one time window preferably corresponds to the beginning and the end of the diastole phase;

Step d) a computing step wherein a 3D cartography of at least one parameter related to coronary blood flow velocity is automatically computed in said imaged volume, based on the sequence of N 3D coronary blood flow images corresponding to the at least one time window identified in step c);

Step e) a locating step wherein at least one point of interest having a predetermined property is located in said sequence of N 3D coronary blood flow images corresponding to the at least one time window identified in step c), based solely on the 3D cartography of step d);

Step f) a quantification step wherein the coronary blood flow velocity is automatically determined at the at least one point of interest of step e) and a predetermined quantification parameter is automatically computed, involving said coronary blood flow velocity; said coronary blood flow velocity being automatically determined at said at least one point of interest based solely on the 3D cartography of step d).

Bibliography (references in the present disclosure are made according to the following numbering:

[1] P. G. Camici, G. d'Amati, O. Rimoldi, Nat. Rev. Cardiol. 12, 48-62 (2015).
[2] S. D. Fihn et al., J. Thorac. Cardiovasc. Surg. 149, e5-23 (2015).
[3] J. A. Ambrose, D. H. Israel, Curr. Opin. Cardiol. 5, 411-416 (1990).
[4] A. Sharma, A. Arbab-Zadeh, J. Nucl. Cardiol. 19, 796-806 (2012).
[5] W. Y. Kim et al., N. Engl. J. Med. 345, 1863-1869 (2001).
[6] T. P. van de Hoef, M. Siebes, J. A. E. Spaan, J. J. Piek, Eur. Heart J. 36, 3312-3319a (2015).
[7] E. J. Velazquez et al., N. Engl. J. Med. 374, 1511-1520 (2016).
[8] Task Force Members et al., Eur. Heart J. 34, 2949-3003 (2013).
[9] A. I. Löffler, J. Bourque, Curr. Cardiol. Rep. 18, 1 (2016).
[10] A. Berrington de Gonzalez et al., Br. J. Cancer. 114, 388-394 (2016).
[11] N. Journy et al., Circ. Cardiovasc. Interv. 11, e006765 (2018).
[12] E. Mace et al., Nat. Methods. 8, 662-664 (2011).
[13] C. Demené et al., IEEE Trans. Med. Imaging. 34, 2271-2285 (2015).
[14] D. Maresca et al., JACC Cardiovasc. Imaging. 11, 798-808 (2018).
[15] WO 2019/158741 A1

What is claimed is:

1. A Method for imaging coronary blood flow of a heart of a living being, said method comprising:
   a) an acquisition wherein unfocused ultrasonic waves are transmitted to the heart by a 2D array ultrasonic transducer and raw data from backscattered ultrasonic waves are acquired by said 2D array ultrasonic transducer;
   b) an imaging wherein a sequence of N 3D volumetric coronary blood flow images of the heart is generated from said raw data, said sequence of N 3D volumetric coronary blood flow images forming an animation showing movements of an imaged volume of the heart;
   c) a determination wherein at least one time window is determined, for which the motion of the heart is minimum;
   d) a computation wherein a 3D cartography of at least one parameter related to coronary blood flow velocity is automatically computed in said imaged volume, based on the sequence of N 3D volumetric coronary blood flow images corresponding to the at least one time window determined in c);
   e) a location wherein at least one point of interest having a predetermined property is located in said sequence of N 3D volumetric coronary blood flow images corresponding to the at least one time window identified in c), based solely on the 3D cartography of d); and
   f) a quantification wherein the coronary blood flow velocity is automatically determined at the at least one point of interest of e) and a predetermined quantification parameter is automatically computed, involving said coronary blood flow velocity; said coronary blood flow velocity being automatically determined at said at least one point of interest based solely on the 3D cartography of d).

2. The method according to claim 1, wherein the at least one time window of determination c) is determined by means of electrocardiography.

3. The method according to claim 1, wherein the at least one time window of c) corresponds to the beginning and the end of the diastole phase and the quantification parameter of f) is chosen amongst flow, maximum speed, average speed or temporal speed profile.

4. The method according to claim 1, further comprising a tracking wherein microbubbles or ultrasound contrast agents are tracked and their trajectory and speed is determined, in a patient that has been previously administered microbubbles or ultrasound contrast agents injected in his vascular system.

5. The method according to claim 1, further comprising automatically quantifying a density of the coronary vessels; and automatically quantifying a blood volume perfused by volume unit; a stenosis is automatically detected by an acceleration of the blood flow velocity; obtaining a coronary flow reserve index by estimating the variation of coronary blood flow velocity in a patient that has been previously administrated with a vasodilator substance; and further comprising an automatic segmentation step of the central cavity.

6. The method according to claim 1, wherein the determination c) comprises:
   i) an imaging wherein a sequence of N 3D volumetric tissue images of the heart are generated from the raw data of a), said sequence of N 3D volumetric tissue images of the heart forming an animation showing movements of the imaged volume of the heart,
   ii) a computing wherein a 3D cartography of at least one parameter related to heart tissue velocity is automatically computed in said imaged volume, based on said sequence of N 3D volumetric tissue images showing movements of the imaged volume of the heart,
   iii) a motion estimation of the heart tissue wherein said at least one point of interest having the predetermined property is located in said sequence of N 3D volumetric tissue images, based solely on the 3D cartography of ii), and wherein the tissue velocity at said at least one point of interest is automatically determined; and iv) the determination wherein said time window is determined, for which the tissue velocity quantified in iii) reaches a minimum velocity.

7. The method according to claim 6, wherein the minimum velocity of iv) is less than 5 cm/s.

8. The method according to claim 4, wherein the microbubbles or ultrasound contrast agents tracking comprises spatiotemporal filtering or machine learning.

9. The method according to claim 1, further comprising performing tissue motion estimation by means of a Doppler estimator or speckle tracking.

10. An apparatus for 4D imaging coronary blood flow of a heart of a living being, said apparatus including at least a 2D array ultrasonic probe and a control system configured to:
   (a) transmit unfocused ultrasonic waves to the heart by the 2D array ultrasonic transducer and acquire raw data from backscattered ultrasonic waves through said 2D array ultrasonic transducer;
   (b) generate a sequence of N 3D volumetric coronary blood flow images of said heart from said raw data, said sequence of N 3D volumetric coronary blood flow images forming an animation showing movements of an imaged volume of the heart;
   (c) identify at least one time window for which the motion of the heart is minimum;
   (d) automatically compute a 3D cartography of at least one parameter related to coronary blood flow velocity in said imaged volume, based on the sequence of N 3D volumetric coronary blood flow images corresponding to the at least one time window identified in (c);
   (e) locate at least one point of interest having a predetermined property in said sequence of N 3D volumetric coronary blood flow images corresponding to the at least one time window identified in (c), based solely on the 3D cartography of (d); and
   (f) automatically determine the coronary blood flow velocity at the at least one point of interest of (e) based solely on the 3D cartography of (d) and automatically compute a predetermined quantification parameter involving said coronary blood flow velocity.

11. The apparatus according to claim 10, wherein in (c), the apparatus is configured to:
   (i) generate a sequence of N 3D volumetric tissue images of the heart from the raw data of (a), said sequence of N 3D volumetric tissue images of the heart forming an animation showing movements of an imaged volume of said imaged volume of the heart,
   (ii) automatically compute a 3D cartography of at least one parameter related to heart tissue velocity in said imaged volume, based on said sequence of N 3D volumetric tissue images showing movements of an imaged volume of the heart,
   (iii) locate said at least one point of interest having the predetermined property in said sequence of N 3D volumetric tissue images, based solely on the 3D cartography of (ii), and automatically determine the tissue velocity at said at least one point of interest;
   (iv) determine said at least one time window for which the tissue velocity quantified in (iii) reaches a minimum velocity.

12. The apparatus according to claim 11, wherein in (c), the apparatus is configured to determine the at least one time window of (c) by means of electrocardiography.

13. A non-transient computer-readable storage medium encoded with instructions which, when executed by a computer, cause the computer to:
   a) transmit unfocused ultrasonic waves to a heart by a 2D array ultrasonic transducer and acquire raw data from backscattered ultrasonic waves through said 2D array ultrasonic transducer;
   b) generate a sequence of N 3D volumetric coronary blood flow images of the heart from said raw data, said sequence of N 3D volumetric coronary blood flow images forming an animation showing movements of an imaged volume of the heart;
   c) identify at least one time window for which the motion of the heart is minimum;
   d) automatically compute a 3D cartography of at least one parameter related to coronary blood flow velocity in said imaged volume, based on the sequence of N 3D volumetric coronary blood flow images corresponding to the at least one time window identified in c);
   e) locate at least one point of interest having a predetermined property in said sequence of N 3D volumetric coronary blood flow images corresponding to the at least one time window identified in step c), based solely on the 3D cartography of step d);
   f) automatically determine the coronary blood flow velocity at the at least one point of interest of e) based solely on the 3D cartography of step d) and automatically compute a predetermined quantification parameter involving said coronary blood flow velocity.

14. The non-transient computer-readable storage medium according to claim 13 wherein the instructions for carrying out c) which, when executed by the computer, causes the computer to:
   (i) generate a sequence of N 3D volumetric tissue images of said heart from the raw data of (a), said sequence of N 3D volumetric tissue images forming an animation showing movements of said imaged volume of the heart,
   (ii) automatically compute a 3D cartography of at least one parameter related to heart tissue velocity in said imaged volume of the heart, based on said sequence of N 3D volumetric tissue images showing movements of the imaged volume of the heart, and
   (iii) locate said at least one point of interest having the predetermined property in said sequence of N 3D volumetric tissue images, based solely on the 3D cartography of (ii), and automatically determining the tissue velocity at said at least one point of interest;
   (iv) determine said at least one time window for which the tissue velocity quantified in (iii) reaches a minimum velocity.

15. The non-transient computer-readable storage medium according to claim 14, wherein the instructions which, when executed by the computer, cause the computer to carry out c) by means of electrocardiography.

* * * * *